(12) United States Patent
Py

(10) Patent No.: US 9,726,314 B2
(45) Date of Patent: *Aug. 8, 2017

(54) ASEPTIC CONNECTOR WITH DEFLECTABLE RING OF CONCERN AND METHOD

(71) Applicant: Dr. Py Institute, LLC, New Milford, CT (US)

(72) Inventor: Daniel Py, Larchmont, NY (US)

(73) Assignee: DR. PY INSTITUTE LLC, New Milford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/217,864

(22) Filed: Mar. 18, 2014

(65) Prior Publication Data

US 2014/0290770 A1   Oct. 2, 2014

Related U.S. Application Data

(63) Continuation of application No. 13/080,537, filed on Apr. 5, 2011, now Pat. No. 8,671,964.
(Continued)

(51) Int. Cl.
*F16L 41/02* (2006.01)
*A61M 39/18* (2006.01)
*A61M 39/26* (2006.01)

(52) U.S. Cl.
CPC ............. *F16L 41/02* (2013.01); *A61M 39/18* (2013.01); *A61M 39/26* (2013.01);
(Continued)

(58) Field of Classification Search
CPC .................. A61M 39/18; A61M 39/26; A61M 2039/267; F16L 41/02; Y10T 137/0318;
(Continued)

(56) References Cited

U.S. PATENT DOCUMENTS 3,916,929 A   11/1975   Brown
4,232,851 A   11/1980   Johnson
(Continued)

FOREIGN PATENT DOCUMENTS

EP   1 260 245 A2   11/2002
EP   0 981 389 B1   12/2003
(Continued)

OTHER PUBLICATIONS

International Search Report and Written Opinion of the International Searching Authority for International Application No. PCT/US2011/31280, May 7, 2011.

*Primary Examiner* — Kevin Lee
(74) *Attorney, Agent, or Firm* — McCarter & English, LLP

(57) ABSTRACT

An aseptic fluid connector having a first connector including a first fluid passageway for receiving a fluid therein; a first port in fluid communication with the first fluid passageway for passage of the fluid therethrough; and a first deflecting member. The first deflecting member includes a first engaging portion radially spaced relative to the first port, and a first valve movable between a closed position and an open position with movement of the first engaging portion between a non-deflected position and a deflected position, respectively. In the non-deflected position, the first valve is located in the closed position forming a fluid-tight seal between the first valve and first port and preventing the passage of fluid therethrough, and in the deflected position, the first valve is located in the open position allowing the aseptic passage of fluid through the first port.

20 Claims, 9 Drawing Sheets

Related U.S. Application Data

(60) Provisional application No. 61/320,857, filed on Apr. 5, 2010.

(52) U.S. Cl.
CPC .. *A61M 2039/267* (2013.01); *Y10T 29/49826* (2015.01); *Y10T 137/0318* (2015.04); *Y10T 137/87925* (2015.04); *Y10T 137/87949* (2015.04); *Y10T 137/87957* (2015.04)

(58) Field of Classification Search
CPC ..... Y10T 137/87957; Y10T 137/87925; Y10T 137/87949
USPC ................ 137/1, 614.03, 614.04; 251/149.1; 604/256
See application file for complete search history.

(56) References Cited

U.S. PATENT DOCUMENTS

| | | |
|---|---|---|
| 4,387,879 A | 6/1983 | Tauschinski |
| 4,673,400 A | 6/1987 | Martin |
| 4,709,725 A | 12/1987 | Morrison |
| 4,752,292 A | 6/1988 | Lopez et al. |
| 4,778,453 A | 10/1988 | Lopez |
| 4,790,832 A | 12/1988 | Lopez |
| 4,816,024 A | 3/1989 | Sitar et al. |
| 4,842,591 A | 6/1989 | Luther |
| 4,846,805 A | 7/1989 | Sitar |
| 4,931,048 A | 6/1990 | Lopez |
| 4,941,517 A | 7/1990 | Galloway |
| 5,199,947 A | 4/1993 | Lopez et al. |
| 5,281,206 A | 1/1994 | Lopez |
| 5,344,414 A | 9/1994 | Lopez et al. |
| 5,492,147 A | 2/1996 | Challender et al. |
| 5,573,516 A | 11/1996 | Tyner |
| 5,685,866 A | 11/1997 | Lopez et al. |
| 5,690,612 A | 11/1997 | Lopez et al. |
| 5,694,686 A | 12/1997 | Lopez et al. |
| 5,695,466 A | 12/1997 | Lopez et al. |
| 5,700,248 A | 12/1997 | Lopez |
| 5,738,663 A | 4/1998 | Lopez |
| 5,791,376 A | 8/1998 | Richmond |
| 5,810,768 A | 9/1998 | Lopez |
| 5,810,792 A | 9/1998 | Fangrow, Jr. et al. |
| 6,039,302 A | 3/2000 | Cote, Sr. et al. |
| 6,039,718 A | 3/2000 | Niedospial, Jr. |
| 6,079,444 A | 6/2000 | Harris et al. |
| 6,245,048 B1 | 6/2001 | Fangrow, Jr. et al. |
| 6,428,520 B1 | 8/2002 | Lopez et al. |
| 6,599,273 B1 | 7/2003 | Lopez |
| 6,634,384 B2 | 10/2003 | Skeens et al. |
| 6,651,955 B2 | 11/2003 | Anderson |
| 6,655,655 B1 | 12/2003 | Matkovich et al. |
| 6,679,529 B2 | 1/2004 | Johnson et al. |
| 6,685,674 B2 | 2/2004 | Douglas et al. |
| 6,695,817 B1 | 2/2004 | Fangrow, Jr. |
| 6,726,672 B1 | 4/2004 | Hanly et al. |
| 6,793,651 B1 | 9/2004 | Bennett |
| 6,837,878 B2 | 1/2005 | Smutney et al. |
| 6,880,801 B2 | 4/2005 | Matkovich et al. |
| 6,892,760 B2 | 5/2005 | Roos et al. |
| 6,916,309 B2 | 7/2005 | Fangrow, Jr. |
| 7,090,191 B2 | 8/2006 | Matkovich et al. |
| 7,099,731 B2 | 8/2006 | Lopez |
| 7,137,974 B2 | 11/2006 | Almasian et al. |
| 7,156,826 B2 | 1/2007 | Ishii et al. |
| 7,309,326 B2 | 12/2007 | Fangrow, Jr. |
| 7,354,427 B2 | 4/2008 | Fangrow |
| 7,396,348 B2 | 7/2008 | Newton et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,523,918 B2 | 4/2009 | Matkovich et al. |
| 7,534,238 B2 | 5/2009 | Fangrow |
| 7,547,300 B2 | 6/2009 | Fangrow |
| 7,569,043 B2 | 8/2009 | Fangrow |
| 7,645,271 B2 | 1/2010 | Fangrow |
| 7,654,995 B2 | 2/2010 | Warren et al. |
| 7,658,205 B1 | 2/2010 | Edelman et al. |
| 7,658,733 B2 | 2/2010 | Fangrow |
| 7,670,322 B2 | 3/2010 | Fangrow, Jr. |
| 7,713,250 B2 | 5/2010 | Harding et al. |
| 7,758,566 B2 | 7/2010 | Simpson et al. |
| 7,803,139 B2 | 9/2010 | Fangrow, Jr. |
| 7,815,614 B2 | 10/2010 | Fangrow, Jr. |
| 7,824,393 B2 | 11/2010 | Fangrow |
| 7,883,499 B2 | 2/2011 | Fangrow |
| 7,892,216 B2 | 2/2011 | Fangrow, Jr. |
| 7,931,615 B2 | 4/2011 | Fangrow, Jr. |
| 8,105,314 B2 | 1/2012 | Fangrow, Jr. |
| 8,409,164 B2 | 4/2013 | Fangrow |
| 8,454,579 B2 | 6/2013 | Fangrow, Jr. |
| 8,522,832 B2 | 9/2013 | Lopez et al. |
| 8,647,310 B2 | 2/2014 | Fangrow, Jr. et al. |
| 8,671,964 B2 * | 3/2014 | Py .................... 137/1 |
| 8,679,090 B2 | 3/2014 | Anderson |
| 8,758,306 B2 | 6/2014 | Lopez et al. |
| 8,956,330 B2 | 2/2015 | Fangrow, Jr. |
| 2002/0133124 A1 | 9/2002 | Leinsing |
| 2003/0020040 A1 | 1/2003 | Anderson |
| 2003/0230340 A1 | 12/2003 | Anderson et al. |
| 2005/0015075 A1 | 1/2005 | Wright et al. |
| 2006/0157971 A1 | 7/2006 | Baldwin et al. |
| 2008/0048436 A1 | 2/2008 | Matkovich et al. |
| 2008/0093571 A1 | 4/2008 | Desecki |
| 2008/0185056 A1 | 8/2008 | Diodati et al. |
| 2009/0050213 A1 | 2/2009 | Biddell et al. |
| 2009/0232586 A1 | 9/2009 | Diodati et al. |
| 2009/0243281 A1 | 10/2009 | Seifert et al. |
| 2010/0007134 A1 | 1/2010 | Elton et al. |

FOREIGN PATENT DOCUMENTS

| | | |
|---|---|---|
| EP | 1 525 023 A1 | 4/2005 |
| EP | 1 297 861 B1 | 9/2006 |
| EP | 1 716 885 A2 | 11/2006 |
| EP | 1 879 642 B1 | 7/2009 |
| EP | 2 121 141 A1 | 11/2009 |
| EP | 2148121 A1 | 1/2010 |
| JP | H09327519 A | 12/1997 |
| JP | 2004195016 A | 7/2004 |
| JP | 2004275472 A | 10/2004 |
| JP | 2008514891 A | 5/2008 |
| WO | 93/11828 | 6/1993 |
| WO | 9850105 A1 | 11/1998 |

* cited by examiner

ASEPTIC CONNECTOR WITH DEFLECTABLE RING OF CONCERN AND METHOD

CROSS-REFERENCE TO RELATED APPLICATIONS

This patent application is a continuation of U.S. patent application Ser. No. 13/080,537, filed Apr. 5, 2011, entitled "Aseptic Connector with Deflectable Ring of Concern and Method," now U.S. Pat. No. 8,671,964, which claims priority to U.S. Provisional Application No. 61/320,857, filed Apr. 5, 2010, the contents of all of which are hereby expressly incorporated by reference in their entireties as part of the present disclosure.

FIELD OF THE INVENTION

The present invention relates to fluid connectors and methods of transferring fluids, and more particularly, relates to aseptic fluid connectors and methods for aseptically transferring fluids.

BACKGROUND INFORMATION

A typical fluid connector includes a male connector that is received within a female connector to place the two connectors in fluid communication with each other. The male and female connectors may be threadedly engaged, snap fit, or otherwise releasably connected to each other to allow for interconnection and disconnection. Each connector is coupled in fluid communication with a respective fluid passageway, such as a tube or fluid chamber, in order to place the fluid passageways in fluid communication with each other and allow the passage of fluids therebetween.

Such fluid connectors typically do not prevent the contamination of fluids passing through them. For example, prior to interconnection of the male and female connectors, the fluid-contacting surfaces thereof can be exposed to the ambient atmosphere and contaminated through contact with airborne germs and/or by contact with contaminated surfaces. One approach to preventing such contamination is to wipe the fluid-contacting surfaces of the male and female connectors with an alcohol wipe or other disinfectant prior to interconnection. One drawback of this approach is that it may not remove all germs on the fluid-contacting surfaces. Another drawback of this approach is that the fluid-contacting surfaces may become contaminated after the wipe is applied but prior to interconnection of the male and female connectors. Yet another drawback of this approach is that it can be time consuming and considered a nuisance, and therefore unreliable in practice.

Accordingly, aseptic or sterile fluids can be subjected to contamination when passed through such prior art connectors. Such contamination can give rise to significant problems. If used in a hospital or other medical facility, such as to transfer sterile drugs or other fluids intended for intravenous injection, for example, any such contamination can lead to viral and other types of infections, serious illnesses, and death. In food processing applications, on the other hand, it may be necessary to connect fluid conduits, for example, in order to transfer sterile or aseptic fluids from one passageway to another. If the fluids are contaminated upon passage through a fluid connector, this can lead to contamination of previously-sterile food products, and if such contaminated products are ingested, they can cause infections and/or illnesses. In industrial applications, it may be necessary to prevent a toxic fluid passing through a connector from contaminating the ambient atmosphere, an operator handling the connector, and/or other surfaces that might be located external to the connector. If the fluid-contacting surfaces of the connector are exposed to human contact, or surfaces that come into human contact, for example, this can lead to possible injury and/or illnesses.

Accordingly, it is an object of the present invention to overcome one or more of the above-described drawbacks and/or disadvantages of the prior art.

SUMMARY OF THE INVENTION

In accordance with a first aspect, the present invention is directed to an aseptic fluid connector comprising a first connector including a first fluid passageway for receiving a fluid therein; a first port in fluid communication with the first fluid passageway for passage of the fluid therethrough; and a first deflecting member. The first deflecting member includes a first engaging portion radially spaced relative to the first port, and a first valve movable between a closed position and an open position with movement of the first engaging portion between a substantially non-deflected position and a deflected position, respectively. In the substantially non-deflected position, the first valve is located in the closed position forming a fluid-tight seal between the first valve and first port and preventing the passage of fluid therethrough, and in the deflected position, the first valve is located in the open position allowing the aseptic passage of fluid through the first port.

In the currently preferred embodiments of the present invention, the aseptic connector further includes a second connector connectable to the first connector. The second connector includes a second fluid passageway for receiving a fluid therein; a second port in fluid communication with the second fluid passageway for passage of the fluid therethrough; and a second deflecting member. The second deflecting member includes a second engaging portion radially spaced relative to the second port, and a second valve movable between a closed position and an open position with movement of the second engaging portion between a substantially non-deflected position and a deflected position, respectively. In the substantially non-deflected position, the second valve is located in the closed position forming a fluid-tight seal between the second valve and second port and preventing the passage of fluid therethrough, and in the deflected position, the second valve is located in the open position allowing the passage of fluid through the second port.

In currently preferred embodiments of the present invention, the first and second connectors are movable between non-connected and connected positions. In the non-connected position, the first and second engaging portions are in their substantially non-deflected positions, and the first and second valves are in their closed positions. In such position, each valve forms a fluid-tight seal between the respective port and ambient atmosphere and prevents external contamination of any fluid-contacting surfaces of the respective port. In the connected position, on the other hand, the first and second engaging portions are in the deflected position and the first and second valves are in the open position to allow sterile fluid flow therebetween.

In currently preferred embodiments of the present invention, each connector further includes a body defining a sealing surface formed adjacent to the respective port, and engageable with the respective valve in the closed position to form a fluid-tight seal between the valve and port. In some such embodiments, each sealing surface is substantially annular, each valve is substantially annular, and in the closed position, each valve engages the respective sealing surface and forms an annular fluid-tight seal therebetween. In some such embodiments, each sealing surface is relatively rigid and each valve is flexible. In the closed position, each valve and respective sealing surface form an interference fit therebetween at the annular fluid-tight seal. In some such embodiments, each engaging portion is formed integral with the respective valve, is radially spaced relative to the respective valve, extends annularly about the respective valve, and extends axially relative to the respective valve. Preferably, each engaging portion and valve are made of an elastic material, such as silicone.

In the currently preferred embodiments of the present invention, the first connector further includes a first body defining a first sealing surface formed adjacent to the first port, and engageable with the first valve in the closed position to form a fluid-tight seal between the first valve and first port. The second connector further includes a second body defining a second sealing surface formed adjacent to the second port, and engageable with the second valve in the closed position to form a fluid-tight seal between the second valve and second port. In some such embodiments, in the non-deflected position, the first valve forms a fluid-tight seal between the first port and ambient atmosphere and prevents external contamination of any fluid-contacting surfaces of the first port. Similarly, the second valve forms a fluid-tight seal between the second port and ambient atmosphere, and prevents external contamination of any fluid-contacting surfaces of the second port. In some such embodiments, the first sealing surface is substantially annular, the first valve is substantially annular, and in the closed position, the first valve engages the first sealing surface and forms an annular fluid-tight seal therebetween. Similarly, the second sealing surface is substantially annular, the second valve is substantially annular, and in the closed position, the second valve engages the second sealing surface and forms an annular fluid-tight seal therebetween. In the currently preferred embodiments, each annular fluid-tight seal extends axially between the respective valve and sealing surface to further prevent the ingress of contaminants through the seal.

Also in the currently preferred embodiments of the present invention, the first sealing surface is relatively rigid, the first valve is flexible, and in the closed position, the first valve and first sealing surface form an interference fit therebetween at the respective annular fluid-tight seal. Similarly, the second sealing surface is relatively rigid, the second valve is flexible, and in the closed position, the second valve and second sealing surface form an interference fit therebetween at the respective annular fluid-tight seal. In some such embodiments, the first engaging portion is formed integral with the first valve, is radially spaced relative to the first valve, extends annularly about the first valve, and extends axially relative to the first valve. Similarly, the second engaging portion is formed integral with the second valve, is radially spaced relative to the second valve, extends annularly about the second valve, and extends axially relative to the second valve. In some such embodiments, each deflecting portion is substantially dome shaped, and each valve extends laterally with respect to the axis of the respective dome-shaped deflecting portion. In some such embodiments, each deflecting portion is substantially cylindrical shaped, and each valve extends substantially normal to an axis of the respective substantially cylindrical shaped deflecting portion. Preferably, the first engaging portion and first valve are made of an elastic material, such as silicone, and the second engaging portion and second valve are made of an elastic material, such as silicone.

In the currently preferred embodiments of the present invention, in the connected position, the first and second engaging portions engage each other and deflect each other into the deflected positions, and the first and second valves are invaginated within the first and second engaging portions into their respective open positions, the first and second ports are in fluid communication with each other, and fluid is permit to flow therebetween.

In the currently preferred embodiments of the present invention, in the connected position, the first and second engaging portions form a substantially fluid-tight seal therebetween. In some such embodiments, in the connected position, the first and second engaging portions extend annularly about the first and second valves and the first and second ports, respectively, and form a substantially fluid-tight seal with respect to ambient atmosphere. In some such embodiments, in the connected position, the first and second valves extend annularly about the first and second ports, respectively, form a substantially fluid-tight seal with respect to ambient atmosphere, and prevent contamination of any fluid-contacting surfaces of the first and second ports.

In some embodiments of the present invention, the first connector is a female connector, and the second connector is male connector that is received within the female connector in the connected position. In some such embodiments, the first connector includes a first connector housing that extends annularly about the first engaging portion and the first valve and extends axially outwardly therefrom. Similarly, the second connector includes a second connector housing that extends annularly about the second engaging portion and the second valve, and extends axially outwardly therefrom, and is receivable within the first connector housing in the connected position. In the connected position, the second connector housing is received within the first connector housing, and the first and second engaging portions and the first and second valves, are located within the second connector housing. In some such embodiments, the first connector includes a first body defining the first port, the second connector includes a second body defining the second port, and in the closed position, a distal portion of the second body is received within a distal portion of the first body.

In some embodiments of the present invention, the first connector includes a plurality of first ports angularly spaced relative to each other, and the second connector includes a plurality of second ports angularly spaced relative to each other. In some embodiments of the present invention, a first fluid conduit is connected in fluid communication with the first connector, and a second fluid conduit is connected in fluid communication with the second connector.

In accordance with another aspect, the present invention is direct to an aseptic connector comprising first means for connecting. The first means includes a first fluid passageway for receiving a fluid therein; second means in fluid communication with the first fluid passageway for the passage of the fluid therethrough; and third means for deflecting. The third means includes fourth means radially spaced relative to the second means for engaging another connector and for deflecting the third means, and fifth means movable between (i) a closed position for sealing the second means by forming a fluid-tight seal between the fifth means and second means and for preventing the passage of fluid therethrough, and (ii) an open position for allowing fluid flow through the second means. The fifth means is movable between the closed and open positions with movement of the fourth means between the substantially non-deflected position and a deflected position, respectively.

In some embodiments of the present invention, the aseptic connector further comprises sixth means for connecting. The sixth means includes a second fluid passageway for receiving a fluid therein; seventh means in fluid communication with the second fluid passageway for passage of the fluid therethrough; and eighth means for deflecting. The eighth means includes ninth means radially spaced relative to the seventh means for engaging another connector and deflecting the eighth means, and tenth means movable between (i) a closed position for sealing the seventh means by forming a fluid-tight seal between the tenth means and seventh means and for preventing the passage of fluid therethrough, and (ii) an open position for allowing fluid flow through the seventh means. The tenth means is movable between the closed and open positions with movement of the ninth means between the substantially non-deflected position and a deflected position, respectively.

In the currently preferred embodiments of the present invention, the first means is a first connector, the second means is a first port, the third means is a first deflecting member, the fourth means is a first engaging portion, the fifth means is a first valve, the sixth means is a second connector, the seventh means is a second port, the eighth means is a second deflecting member, the ninth means is a second engaging portion, and the tenth means is a second valve.

In accordance with another aspect, the present invention is directed to a method comprising the following steps:

providing a first connector including a first valve hermetically sealing in a normally closed position a first port in fluid communication with a first fluid passageway, and a sterile fluid in fluid communication with the first fluid passageway;

connecting the first connector to a second connector including a second port in fluid communication with a second fluid passageway;

during the connecting step, deflecting the first valve from the normally closed position to an open position, and placing the first port in fluid communication with the second port;

allowing a flow of sterile fluid through the first and second ports; and during the preceding steps, maintaining the first and second ports hermetically sealed with respect to ambient atmosphere and thereby preventing contamination of any fluid-contacting surfaces of the first and second ports and of the sterile fluid flowing therethrough.

In some embodiments of the present invention, the first connector includes a first valve and a first deflecting member, and the second connector includes a second valve and a second deflecting member. The deflecting step includes placing the first and/or second deflecting members into engagement with the other, deflecting the first and second deflecting members and, in turn, moving the first and second valves from normally closed positions to open positions and, in turn, placing the first and second ports in fluid communication with each other.

In some such embodiments, the method further comprises the step of forming a fluid tight seal between (i) the first and second deflecting members, and/or (ii) the first and second valves, when in the connected and open positions, to hermetically seal the first and second ports with respect to ambient atmosphere, and thereby prevent contamination of any fluid-contacting surfaces of the first and second ports and of the sterile fluid flowing therethrough.

In some such embodiments, during the connecting step, the first and second deflecting members resiliently engage each other, and invaginate the first and second valves into the open position and into contact with each other to form an annular, fluid-tight seal therebetween.

One advantage of the present invention is that when not connected, the valve maintains the port hermetically sealed with respect to ambient atmosphere and prevents contamination of any fluid-contacting surfaces connector. Then, when connected, the valve and/or deflecting member maintains the port and any fluid-contacting surfaces hermetically sealed with respect to ambient atmosphere. Accordingly, the present invention is particularly advantages for fluid transfer of aseptic or sterile fluids. For example, two fluid conduits can be interconnected with the connector of the present invention, and an aseptic or sterile fluid passed therethrough, without contaminating the aseptic or sterile fluid.

Other objects and advantages of the present invention, and/or of the currently preferred embodiments thereof, will become more readily apparent in view of the following detailed description of the currently preferred embodiments and accompanying drawings.

DETAILED DESCRIPTION OF THE CURRENTLY PREFERRED EMBODIMENTS

Figure 1:
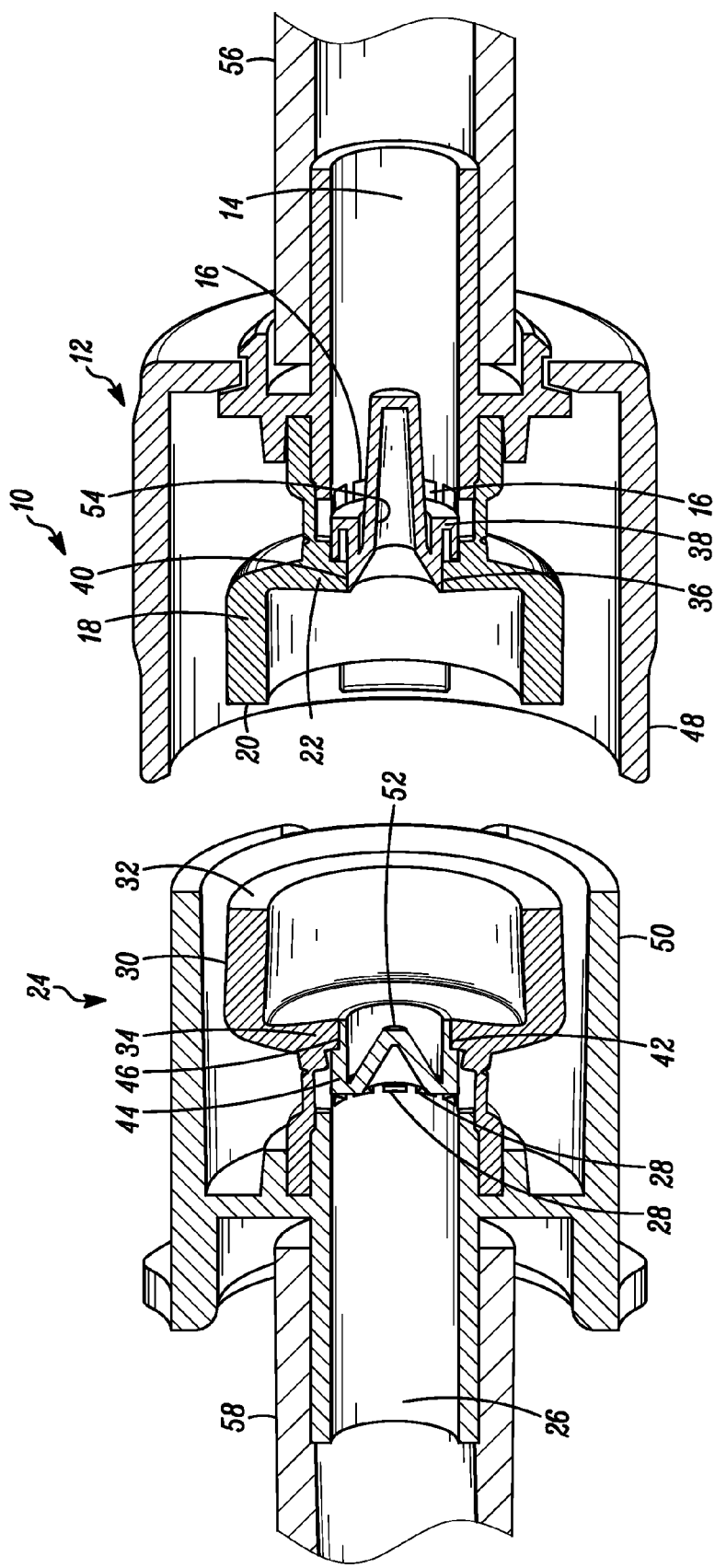
FIG. 1 is a perspective, cross-sectional view of a connector embodying the present invention showing the male and female connectors in a non-connected state with the valves of the connectors in their closed positions hermetically sealing the interiors of the connectors from ambient atmosphere.

In FIG. 1, a connector embodying the present invention is indicated generally by the reference numeral 10. The connector 10 comprises a first or female connector 12 including a first fluid passageway 14 for receiving a fluid therein; a plurality of first ports 16 in fluid communication with the first fluid passageway 14 for passage of the fluid therethrough; and a first deflecting member 18. The first deflecting member 18 includes a first engaging portion 20 radially spaced relative to the first port 16, and a first valve 22 movable between a closed position (FIG. 1) and an open position (FIG. 3) with movement of the first engaging portion 20 between a substantially non-deflected position (FIG. 1) and a fully deflected position (FIG. 3), respectively. In the substantially non-deflected position (FIG. 1), the first valve 22 is located in the closed position forming a fluid-tight seal between the first valve and first ports 16 and preventing the passage of fluid therethrough. In the fully deflected position (FIG. 3), the first valve 22 is located in the fully open position allowing the aseptic passage of fluid through the first ports 16.

The aseptic connector 10 further includes a second or male connector 24 connectable to the first or female connector 12. The second connector 24 includes a second fluid passageway 26 for receiving a fluid therein; a plurality of second ports 28 in fluid communication with the second fluid passageway 26 for the passage of the fluid therethrough; and a second deflecting member 30. The second deflecting member 30 includes a second engaging portion 32 radially spaced relative to the second ports 28, and a second valve 34 movable between a closed position (FIG. 1) and a fully open position (FIG. 3) with movement of the second engaging portion 32 between a substantially non-deflected position (FIG. 1) and a fully deflected position (FIG. 3), respectively. In the substantially non-deflected position (FIG. 1), the second valve 34 is located in the closed position forming a fluid-tight seal between the second valve 34 and second ports 28 and preventing the passage of fluid therethrough. In the fully deflected position (FIG. 3), the second valve 34 is located in the fully open position allowing the passage of fluid through the second ports 28.

Figure 2A:
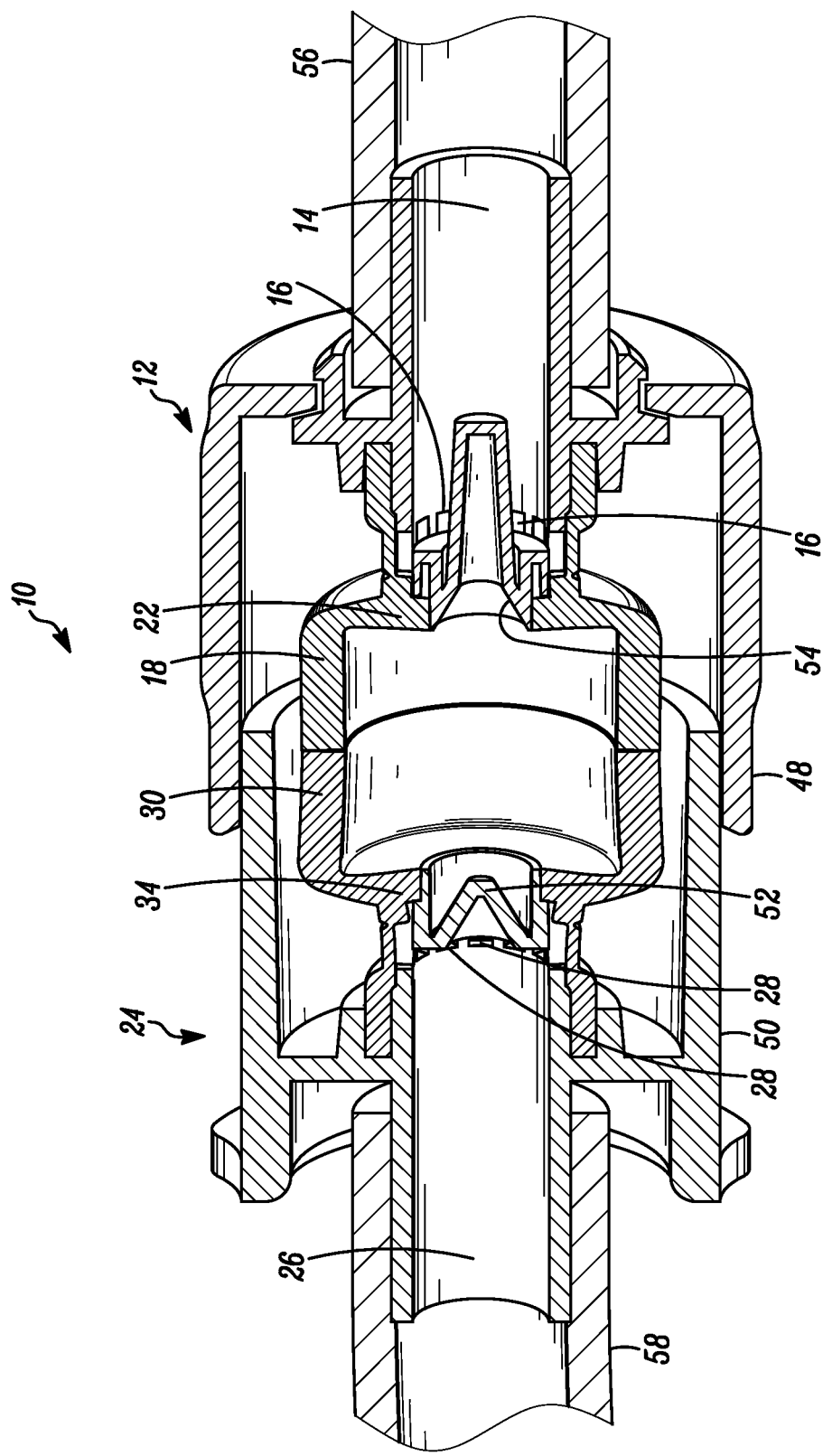
FIG. 2A is a perspective, cross-sectional view of the connector of FIG. 1 showing the start of an interconnection of the male and female connectors wherein the male connector housing is initially received within the female connector housing and the engaging surfaces of the opposing deflecting members are in peripheral contact with each other.
Figure 2B:
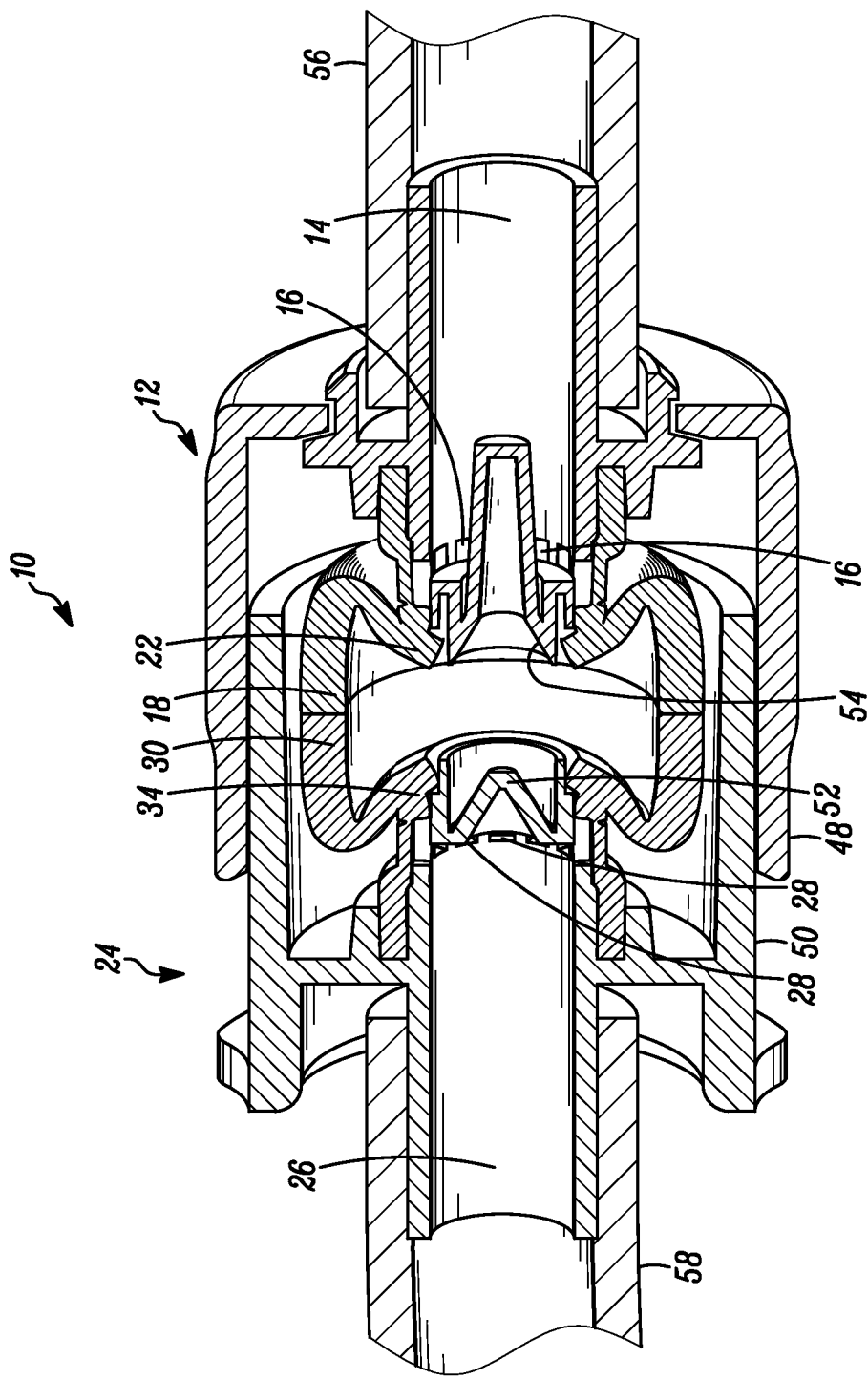
FIG. 2B is a perspective, cross-sectional view of the connector of FIG. 2A showing progression of the interconnection of the male and female connectors wherein the opposing deflecting members are further pressed into engagement with each other forming an annular fluid-tight seal therebetween, and the valves are initially deflected away from the respective sealing surfaces to initiate opening of the valves.
Figure 2C:
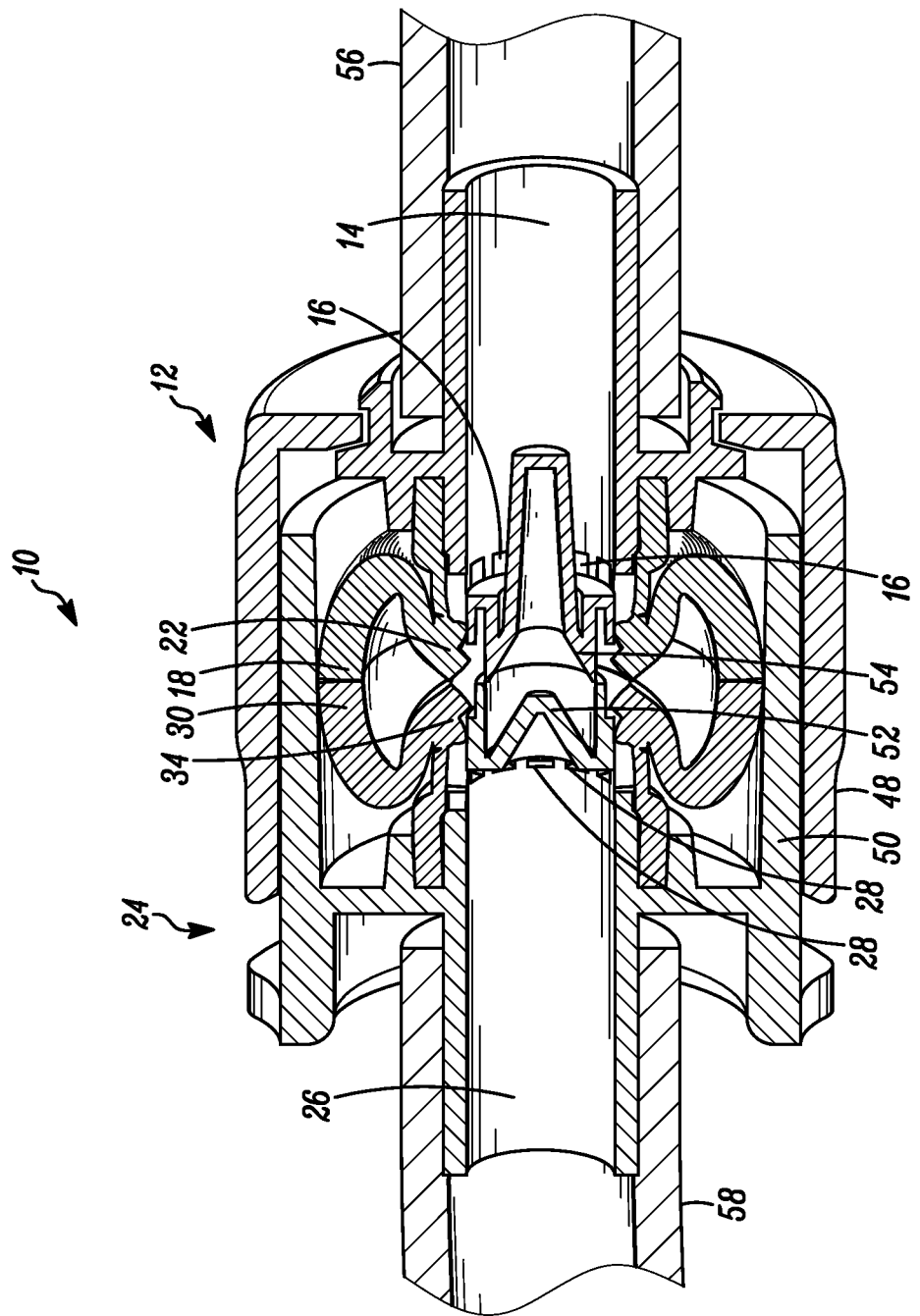
FIG. 2C is a perspective, cross-sectional view of the connector of FIG. 2B showing further progression of the interconnection of the male and female connectors, wherein the deflecting members are further deflected into engagement with each other, the valves are further moved radially away from the respective sealing surfaces to further open the sterile flow path between the ports of the male and female connectors.
Figure 2D:
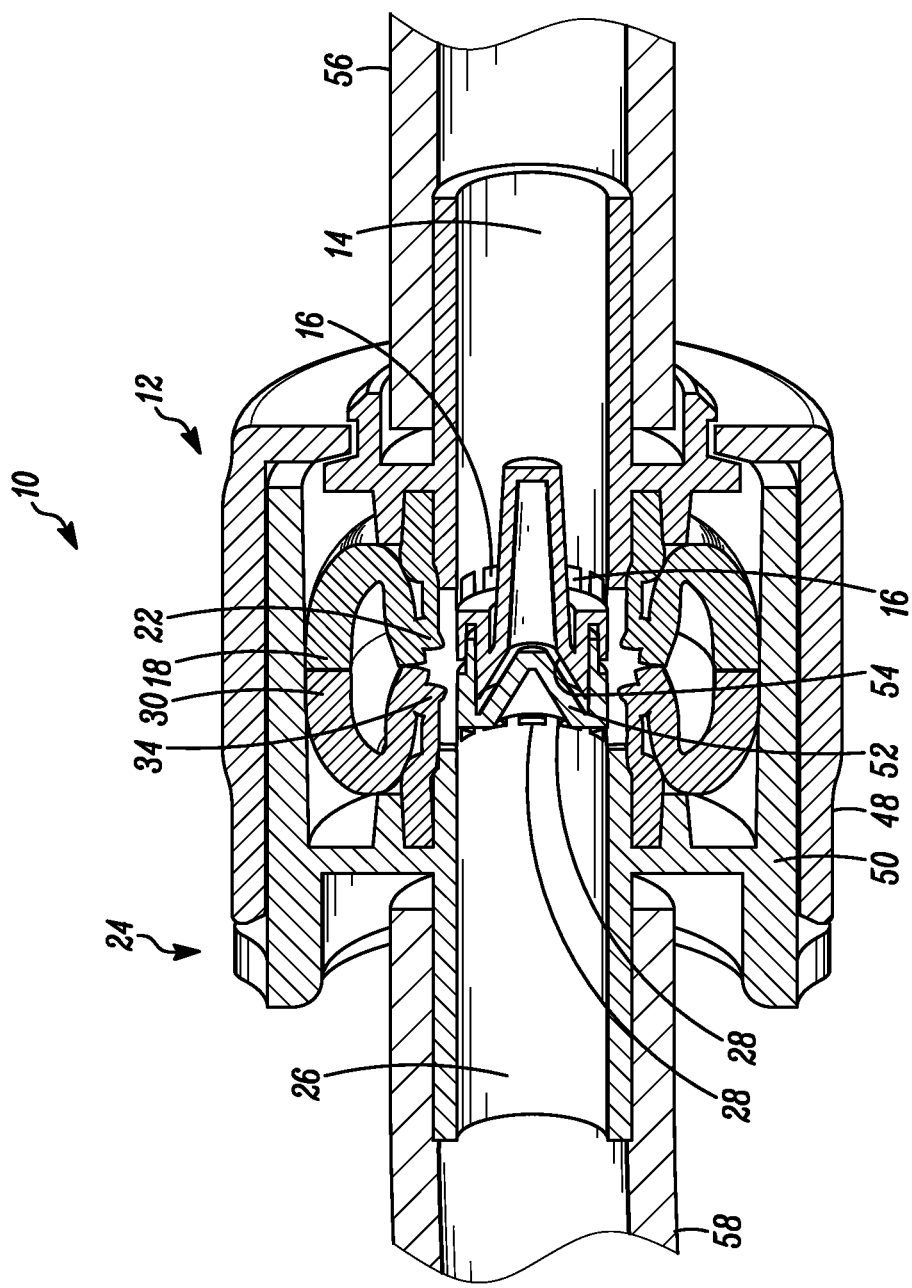
FIG. 2D is a perspective, cross-sectional view of the connector of FIG. 2C showing further progression of the interconnection of the male and female connectors, wherein the opposing valves of the connectors are deflected or invaginated into contact with each other to initiate forming a fluid-tight seal therebetween and to further open the sterile flow path between the ports of the connectors.
Figure 2E:
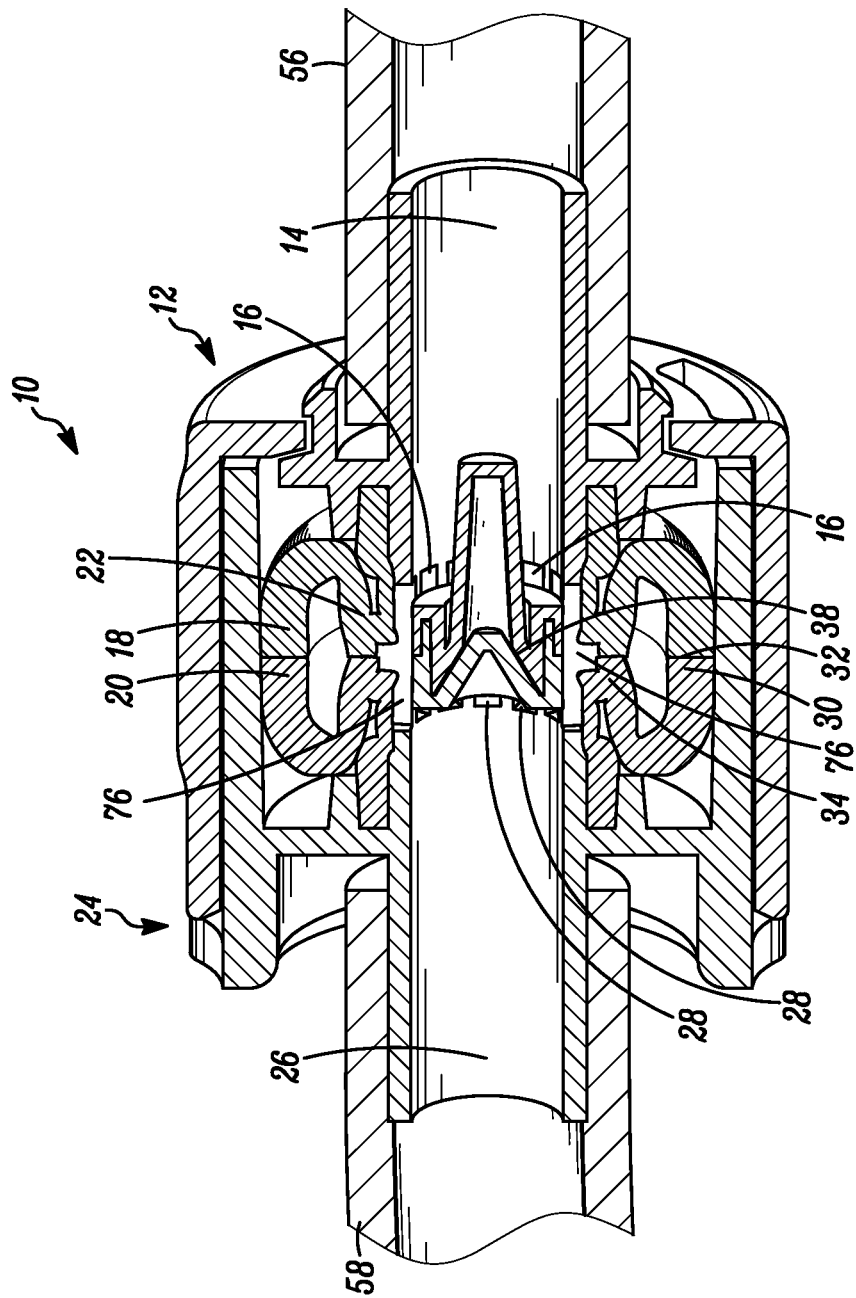
FIG. 2E is a perspective, cross-sectional view of the connector of FIG. 2D showing further progression of the interconnection of the male and female connectors, wherein both the opposing deflecting members and opposing valves of the connectors are pressed into full engagement with each other to form annular fluid-tight seals therebetween and to further open the sterile flow path between ports of the connectors.
Figure 3:
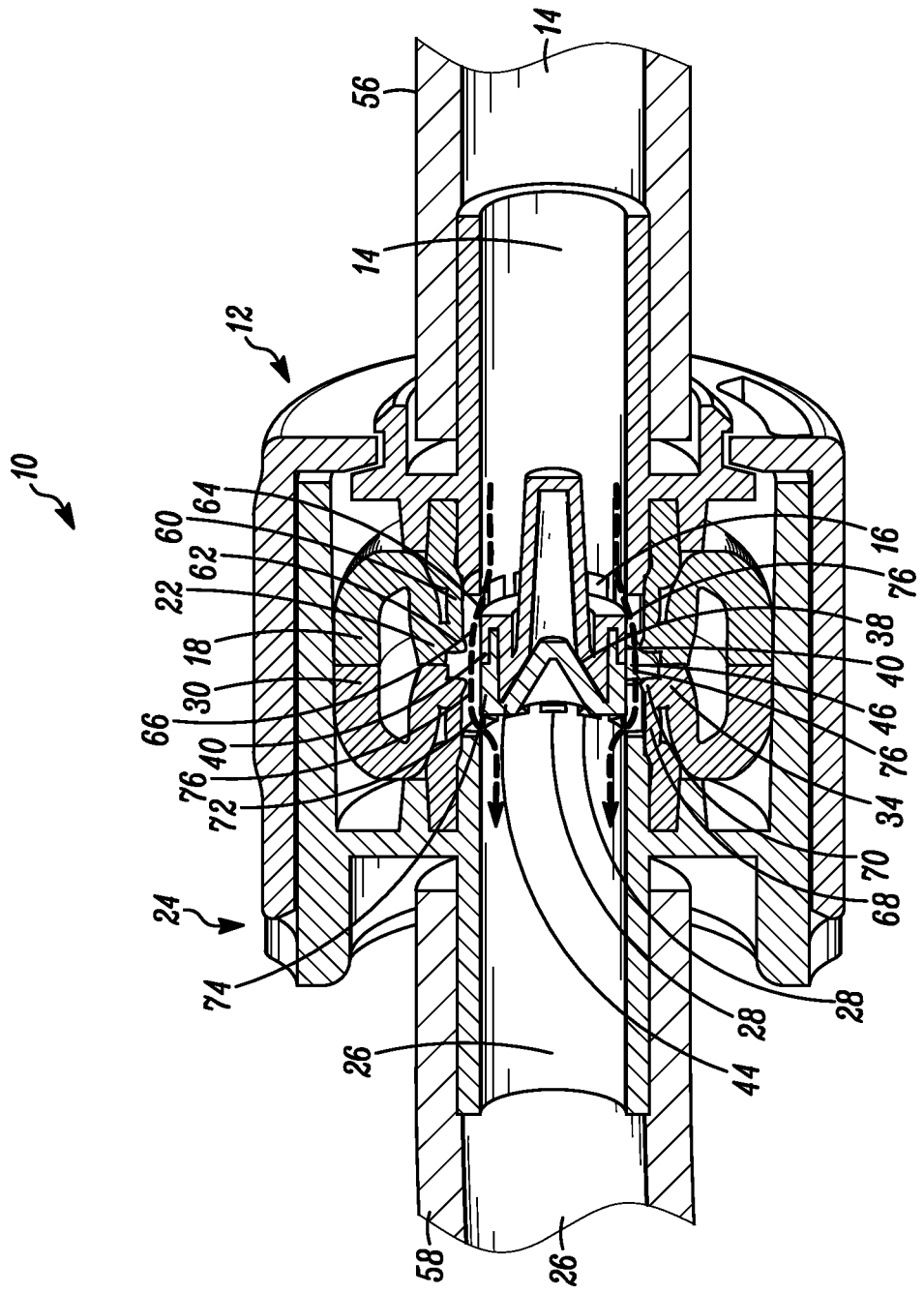
FIG. 3 is a perspective, cross-sectional view of the connector of FIG. 2E showing full interconnection of the male and female connectors, wherein an annular fluid-tight seal is formed between the opposing valves of the connectors to seal the sterile fluid flow path between the ports of the connectors, and the ring of concern within the substantially cylindrical deflecting members is sealed with respect to the sterile fluid flow path to prevent any contamination of the sterile fluid flow path or the fluid flowing through the connector.

As shown in FIGS. 1 through 3, the first and second connectors 12, 24 are movable into engagement with each between non-connected and connected positions. In the non-connected position (FIG. 1), the first and second engaging portions 20, 32 are in the substantially non-deflected positions, and the first and second valves 22, 34 are in the closed positions. In the fully connected position (FIG. 3), the first and second engaging portions 20, 32 are engaged with each other in the fully deflected positions, and the first and second valves 22, 34 are in their fully open positions.

In the non-deflected position (FIG. 1), the first valve 12 forms a fluid-tight seal 36 between the first ports 16 and ambient atmosphere and prevents external contamination of any fluid-contacting surfaces of the first ports 16. The first connector 12 further includes a first body 38 defining a first sealing surface 40 formed adjacent to the first ports 16, and engageable with the first valve 22 in the closed position to form a fluid-tight seal between the first valve and first ports. As can be seen, the first sealing surface 40 is substantially annular, the first valve 22 is substantially annular, and in the closed position, the first valve 22 engages the first sealing surface 40 and forms an annular fluid-tight seal 36 therebetween. The first sealing surface 40 is relatively rigid and the first valve 22 is flexible. In the closed position, the first valve 22 and first sealing surface 40 form an interference fit therebetween at the annular fluid-tight seal 36. As can be seen, the first engaging portion 20 is formed integral with the first valve 22, is radially spaced relative to the first valve 22, extends annularly about the first valve 22, and extends axially relative to the first valve 22. The integral first engaging portion 20 and first valve 22 are made of an elastic material, such as silicone.

In the non-deflected position (FIG. 1), the second valve 24 forms a second fluid-tight seal 42 between the second ports 28 and ambient atmosphere, and prevents external contamination of any fluid-contacting surfaces of the second ports 28. The second connector 24 further includes a second body 44 defining a second sealing surface 46 formed adjacent to the second ports 28, and engageable with the second valve 34 in the closed position to form a fluid-tight seal between the second valve and second ports. As can be seen, the second sealing surface 46 is substantially annular, the second valve 34 is substantially annular, and in the closed position (FIG. 1), the second valve 34 engages the second sealing surface 46 and forms an annular fluid-tight seal 42 therebetween. The second sealing surface 46 is relatively rigid and the second valve 34 is flexible. In the closed position, the second valve 34 and second sealing surface 46 form an interference fit therebetween at the annular fluid-tight seal 42. As can be seen, the second engaging portion 32 is formed integral with the second valve 34, is radially spaced relative to the second valve 34, extends annularly about the second valve 34, and extends axially relative to the second valve 34. The integral second engaging portion 32 and second valve 34 are made of an elastic material, such as silicone.

Each first engaging portion 20, 32 is formed integral with the respective valve 22, 34, is radially spaced relative to the respective valve, extends annularly about the respective valve, and extends axially relative to the respective valve. In the illustrated embodiment, each deflecting portion 20, 32 is substantially dome shaped, and each valve 22, 34 extends laterally with respect to the axis of the respective dome-shaped deflecting portion. Also in the illustrated embodiment, each deflecting portion 20, 32 is substantially cylindrical shaped, and each valve 22, 34 extends substantially normal to an axis of the respective substantially cylindrical-shaped deflecting portion. As indicated above, each engaging portion 20, 32 and integral valve 22, 34 are made of a flexible or elastic material, such as silicone.

It will be understood that the first and second integral valves 22, 34 are formed of any suitable flexible or elastic material. In some embodiments, a suitable elastic material includes silicone, a vulcanized latex and/or a vulcanized rubber. In at least some embodiments, the first and second integral valves 22, 34 are formed of a material having a substantially predetermined creep. Compression set measures the ability of elastomeric materials to maintain elastic properties after prolonged compressive stress and can be used as a measurement of the material's creep property. In some embodiments, the material for the first and second integral valves 22, 34 is selected from materials having a compression set value within the range of about 0% to about 50% (by ASTM D412), and preferably within the range of about 0% to about 25%. In some embodiments, the integral valves 22, 34 form an interference fit with sealing surfaces 40, 46 in the closed position. In the open position, the integral valves 22, 34 are deflected away from sealing surfaces 40, 46. The integral valves 22, 34 are capable of being maintained in either the open or closed positions for substantial periods of time. In some embodiments, the integral valves 22, 34 are maintained in the open position for about 6, 12, 18, 24, 48 or 72 hours, and because of their relatively low creep property, they remain capable of sealingly engaging the sealing surfaces 40, 46 in the closed position thereafter.

As shown in FIGS. 2E and 3, in the fully connected position, the first and second engaging portions 20, 32 engage each other and deflect each other into the deflected positions, and the first and second valves 22, 34 are invaginated within the first and second engaging portions 20, 32 into their fully open positions, the first and second ports 16, 28 are in fluid communication with each other, and as indicated by the broken line arrows in FIG. 3, fluid is permitted to flow through a sterile flow path therebetween that is hermetically sealed with respect to ambient atmosphere. In the fully connected position, the first and second engaging portions 20, 32 form a substantially fluid-tight seal therebetween. The first and second engaging portions 20, 32 extend annularly about the first and second valves 22, 34 and the first and second ports 16, 28, respectively, and form a substantially fluid-tight seal with respect to ambient atmosphere. Also in the fully connected position, the first and second valves 22, 34 extend annularly about the first and second ports 16, 28, respectively, are invaginated or deflected into contact with each other to form a substantially fluid-tight seal therebetween and with respect to ambient atmosphere, and to prevent contamination of any fluid-contacting surfaces of the first and second ports when the valves are in the fully open position. As can be seen, any germs or other contaminants located on or within the deflecting members 18, 30 (i.e., each deflecting member is a deflecting ring of concern), are hermetically sealed within the engaged deflecting members, and thus prevented by the annular, fluid-tight seal between the engaged, opposing valves 22, 34 from contacting any sterile fluid flowing through the connector.

The first or female connector 12 includes a first or female connector housing 48 that extends annularly about the first deflecting member 18 and the first valve 22 and extends axially outwardly therefrom to enclose the respective deflecting member and valve. Similarly, the second or male connector 24 includes a second or male connector housing 50 that extends annularly about the second deflecting member 30 and the second valve 34, and extends axially outwardly therefrom. As shown in FIGS. 2A through 3, the second or male connector housing 50 is receivable within the first or female connector housing 48 to interconnect and place the two connectors in fluid communication with each other. In the connected positions, the second or male connector housing 50 is received within the first or female connector housing 48, and the first and second engaging portions 20, 32 and the first and second valves 22, 34, are located within the second or male connector housing 50. The first body 38 of the first connector 12 defines the first ports 16, and the second body 44 of the second connector 24 defines the second ports 28. As shown in FIGS. 2E and 3, in the fully closed position, a distal portion 52 of the second body 44 is received within a distal portion 54 of the first body 38 to facilitate aligning the first and second connectors and retaining them in the fully closed position. As may be recognized by those of ordinary skill in the pertinent art based on the teachings herein, the first and second connectors 12, 24 can be releasably connected to each other in any of numerous different ways that are currently known, or that later become known, such as by a threaded connection, snap fit, or other releasable interconnection.

In the illustrated embodiment, the first connector 12 includes a plurality of first ports 16 angularly spaced relative to each other, and the second connector 24 includes a plurality of second ports 28 angularly spaced relative to each other. A first fluid conduit 56 is connected in fluid communication with the first fluid passageway 14 of the first connector 12, and a second fluid conduit 58 is connected in fluid communication with the second fluid passageway 26 of the second connector 24. As may be recognized by those of ordinary skill in the pertinent basted on the teachings herein, the ports may take any of numerous different configurations that are currently known, or that later become known. For example, each connector may include only one port, more than one port, and/or one connector may have a different number and/or configuration of ports than the other connector. For example, one connector may have fewer angularly-elongated ports. Similarly, the first and second connectors may or may not be connected to tubes as shown, but rather may be connected to any of numerous different types of fluid sources, receptacles or devices that are currently known, or that later become known.

As shown in FIG. 1, in the non-connected, closed position, each annular fluid-tight seal 36, 42 extends axially between the respective valve 22, 34 and sealing surface 40, 46 to further prevent the ingress of contaminants through the seal. Each sealing surface 40, 46 is relatively rigid, each valve 22, 34 is flexible, and in the closed position, each valve 22, 34 and respective sealing surface 40, 46 form an interference fit therebetween at the respective annular fluid-tight seal 36, 42.

As shown typically in FIG. 3, the first connector includes a first axially and annularly extending base 60 that overlies the first ports 16. A first annular, deflectable joint 62 extends between the first base 60 and first valve 22 to facilitate movement of the first valve 22 between the closed and open positions. The first body 38 defines an annular and axially-extending first base surface 64 that is formed contiguous to the first ports 16, and a first step 66 extending between the base surface 64 and first sealing surface 40. In the illustrated embodiment, the first step 66 is oriented substantially normal the first base surface 64 and first sealing surface 40.

Similar to the first connector 12, and as shown typically in FIG. 3, the second connector 24 includes a second axially and annularly extending base 68 that overlies the second ports 28. A second annular, deflectable joint 70 extends between the second base 68 and second valve 34 to facilitate movement of the second valve 34 between the closed and open positions. The second body 44 defines an annular and axially-extending second base surface 72 that is formed contiguous to the second ports 28 and a second step 74 extending between the base surface 72 and the second sealing surface 46. In the illustrated embodiment, the second step 74 is oriented substantially normal the second base surface 72 and second sealing surface 46.

In the closed position of the first connector 12 (FIG. 1), the first base 60 sealingly engages the first base 64 of the first valve body 38 to form a fluid-tight seal therebetween, the first step 64 is received within, and sealingly engages the first step 66 of the first body 38 to further effectuate a fluid-tight seal, and the first valve 22 sealingly engages the first sealing surface 40 to effectuate the fluid-tight seal between the valve and body. Similarly, in the closed position of the second connector 24, the second base 68 sealingly engages the second base 72 of the second valve body 44 to form a fluid-tight seal therebetween, the second step 70 is received within, and sealingly engages the second step 74 of the second body 44 to further effectuate a fluid-tight seal, and the second valve 34 sealingly engages the second sealing surface 46 to effectuate the fluid-tight seal between the valve and body. As can be seen, in the normally-closed position, all external fluid-contacting surfaces of the first connector body 38 and second connector body 44 are hermetically sealed within the first and second valves 22 and 34, respectively. In the fully connected, open position, on the other hand (FIGS. 2E and 3), the valves 22, 34 are deflected or invaginated into the fully open position into engagement with each other, and thus moved radially away from the respective sealing surfaces 40, 46, the deflecting joints 62, 70 are deflected radially away from the respective steps 64, 72, and the bases 60, 68 are deflected radially away from the respective body base surfaces 64, 72, to thereby define an annulary, axially-extending fluid passageway 76 extending between the two connectors. As indicated by the broken line arrows in FIG. 3, in the connected, fully open position, fluid is permitted to flow from the first fluid passageway 14, through the plurality of ports 16, through the annular, axially-extending passageway 76, through the plurality of second ports 28, and into the second passageway 26. If desired, the fluid may flow in the opposite direction. The annular, axially-extending passageway 76 is hermetically sealed with respect to both the deflectable ring of concern (i.e., the surfaces of the deflecting members 18, 30) and ambient atmosphere by abutting engagement of the first and second valves 22, 34. As can be seen, the fluid passing between the two connectors is maintained sealed with respect to ambient atmosphere, and the surfaces of the connectors that contact such fluid likewise are sealed with respect to ambient atmosphere to thereby maintain the fluid sterile and hermetically sealed with respect to ambient atmosphere.

Figure 4A:
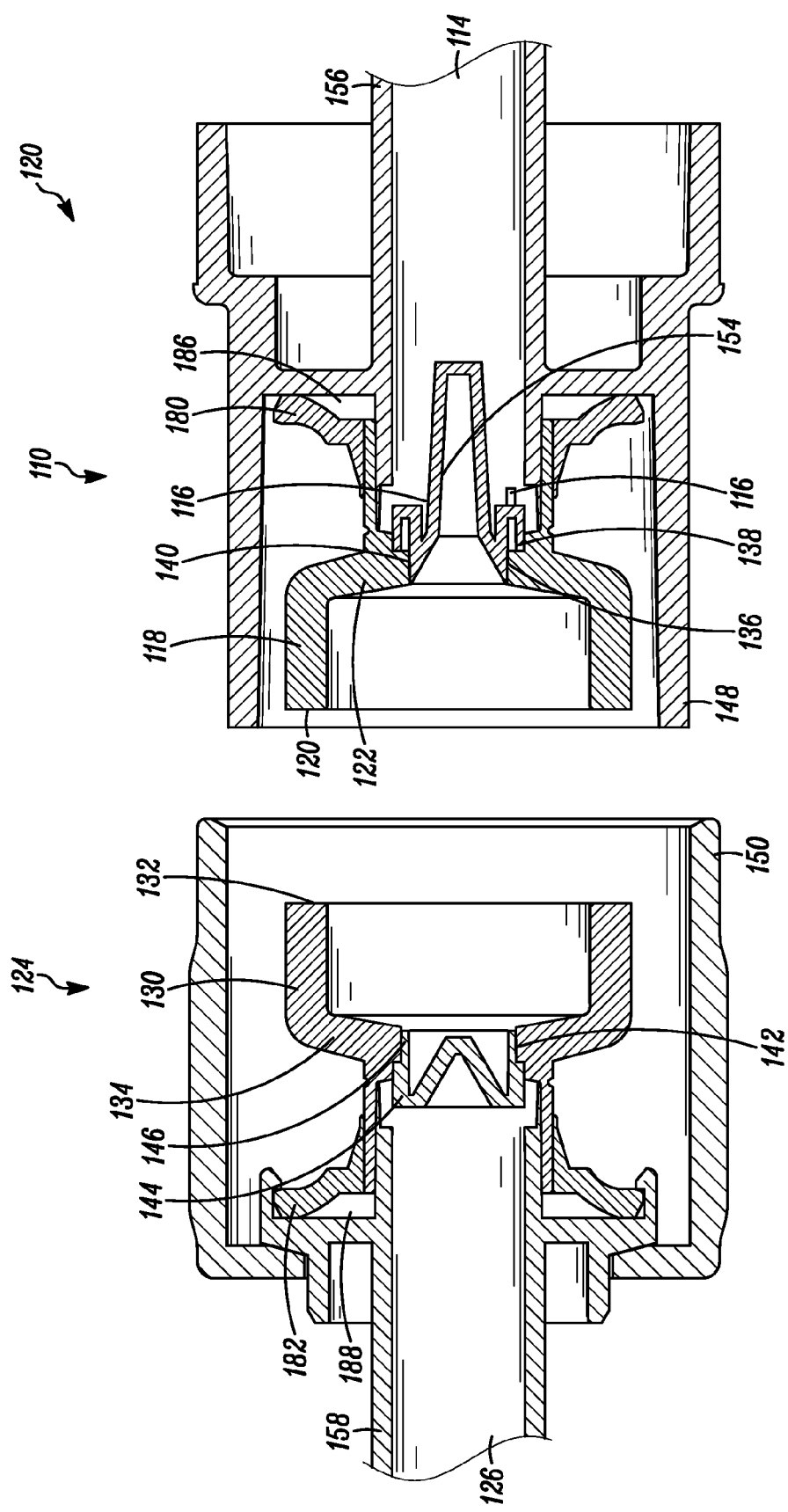
FIG. 4A is a cross-sectional view of another embodiment of a connector of the present invention showing the male and female connectors in a non-connected state with the valves of the connectors in their closed positions hermetically sealing the interiors of the connectors from ambient atmosphere, the connector further having a pair of supports coupled to the male and female connectors for enhanced durability.

Turning to FIG. 4A, another embodiment of a connector of the present invention is indicated generally by the reference numeral 110. The connector 110 is substantially the same as the connector 10 described above, and therefore like reference numerals preceded by the numeral "1" are used to indicate like elements. The primary difference of the connector 110 in comparison to connector 10 is that it includes first and second supports 180, 182 located between the bases of the first and second housings 148, 150 and the first and second valves 122, 134, respectively. The first and second supports 180, 182 may be molded with the bases of the first and second integral valves 122, 134, respectively. In some embodiments, the first and second supports are co-molded or overmolded with the first and second integral valves 122, 134. The first and second supports 180, 182 are snap fit into first and second recesses 186, 188, respectively, provided in the bases of the first and second housings 148, 150, respectively. In the illustrated embodiments, the supports 180, 182 are ring-shaped; however, as may be recognized by those of ordinary skill in the pertinent art, they may take any of numerous different shapes and/or configurations that are currently known or later become known.

Figure 4B:
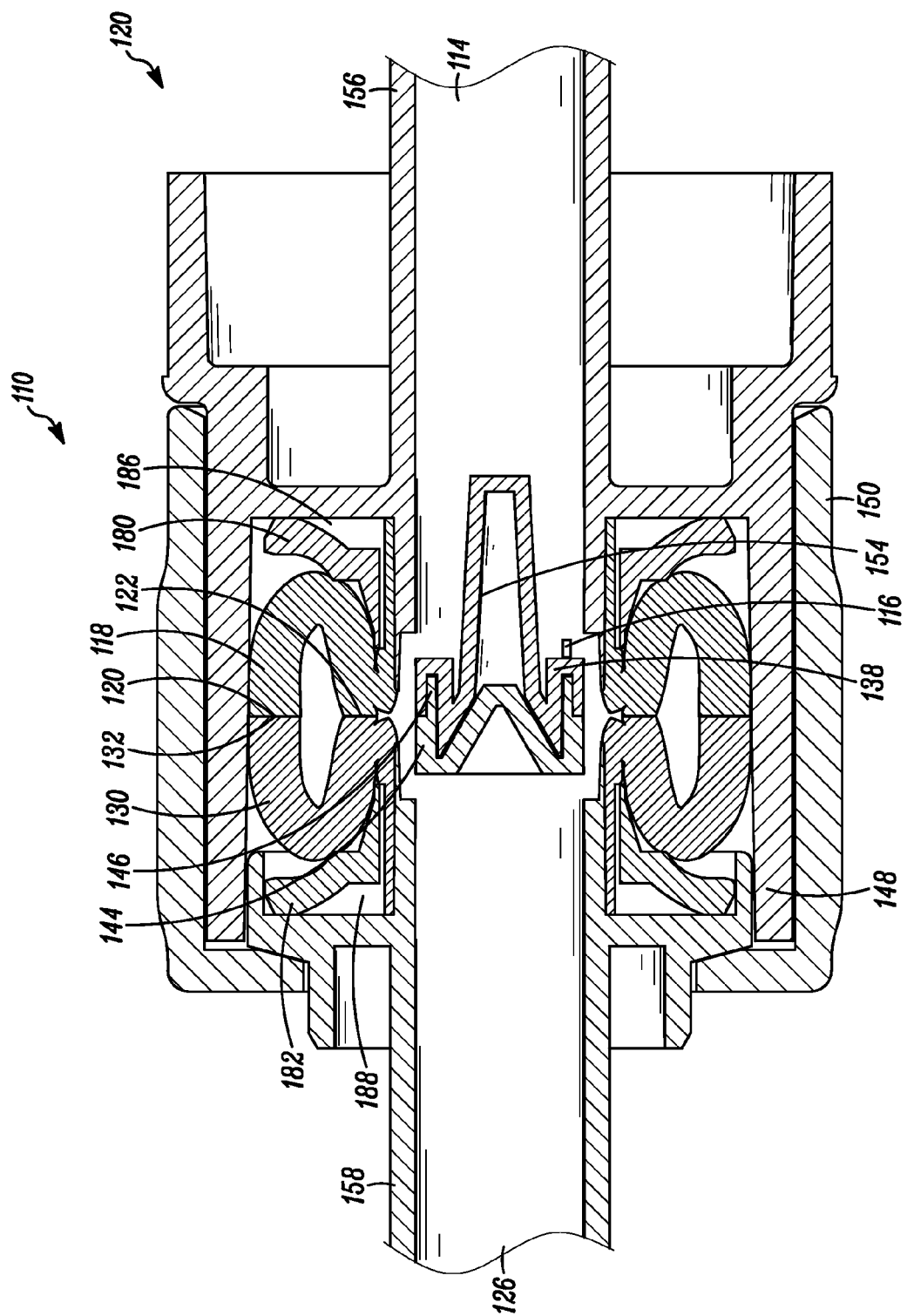
FIG. 4B is a cross-sectional view of the connector of FIG. 4A showing full interconnection of the male and female connectors, wherein an annular fluid-tight seal is formed between the opposing valves of the connectors to seal the sterile fluid flow path between the ports of the connectors, and the ring of concern within the substantially cylindrical deflecting members is sealed with respect to the sterile fluid flow path to prevent any contamination of the sterile fluid flow path or the fluid flowing through the connector.

FIG. 4B is a cross-sectional view of the connector of FIG. 4A showing full interconnection of the male and female connectors. As seen in FIG. 4B, the first and second supports 180, 182 bolster the base of the first and second integral valves 122, 134 and increase the structural integrity and durability of the connector 110 in the open position. In the open, interconnected position, the first and second supports 180, 182 abut the integral valves 122, 134 to prevent failure of the valves. Another embodiment of the first and second supports 180, 182 is that they prevent the first and second integral valves 122, 134 from bending or deforming beyond a maximum, open or deflected position.

The connectors of the present invention have numerous different applications in any of numerous different fields. For example, the connectors may be used to interconnect IV tubing, pouches and tubing, filling tanks and/or filling machines, and any of numerous other applications requiring fluid connections. As can be readily appreciated, the connectors of the present invention are particularly well suited for applications requiring an aseptic or sterile connection, or applications that require the prevention of any contact with the fluid being transferred (such as a toxic fluid).

As may be recognized by those of ordinary skill in the pertinent art based on the teachings herein, numerous changes, modifications and improvements may be made to the above-described and other embodiments of the present invention without departing from the scope of the invention as defined in the appended claims. For example, the ports, valves, engaging portions, deflecting members, connector bodies, connector housings and means for releasably or otherwise connecting the connectors, may take any of numerous different configurations that are currently known, or that later become known. In addition, not all elements or all features disclosed herein are necessary, and if desired, additional elements or features may be added. Further, the elements or components of the connectors may be made of any of numerous different materials that are currently known, or that later become known. Still further, the connectors may be used to transport any of numerous different fluids that are currently known, or that later become known, such as drugs, pharmaceuticals, vaccines, ophthalmic products, creams, ointments, gels, beverages or food products, such as dairy, milk, cream, infant formula, chocolate, and industrial products, such as industrial liquids or gases. Still further, only one of the two connectors may require a valve (e.g., if only one side of the connection need be aseptic or sterile), and thus one connector (male or female) may be a conventional connector or may different from the other connector. Accordingly, this detailed description of the currently preferred embodiments is to be taken in an illustrative, as opposed to a limiting sense.

What is claimed is:

1. An aseptic fluid connector comprising:
a first connector including:
a first fluid passageway for receiving a fluid therein;
a first port in fluid communication with the first fluid passageway for passage of the fluid therethrough; and
a first member, configurable between a first configuration preventing the passage of fluid through the first port and hermetically sealing all fluid-contacting surfaces of the first connector with respect to the ambient atmosphere for preventing external contamination of said surfaces, and a second configuration defining a first aseptic passageway to allow the aseptic passage of fluid through the first port and through the first aseptic passageway; and
a second connector connectable to the first connector and including:
a second fluid passageway for receiving a fluid therein;
a second port in fluid communication with the second fluid passageway for passage of the fluid therethrough; and
a second member, configurable between a first configuration preventing the passage of fluid through the second port and hermetically sealing all fluid-contacting surfaces of the second connector with respect to the ambient atmosphere for preventing external contamination of said surfaces, and a second configuration defining a second aseptic passageway to allow the aseptic passage of fluid therethrough and through the second port,
wherein the second member includes a deflecting member including an engaging portion and movable between a substantially non-deflected position and a deflected position, wherein in the substantially non-deflected position the second member is in its respective first configuration, and in the deflected position, the second member is in its respective second configuration.

2. The aseptic connector as defined in claim 1, wherein the first and second connectors are movable between non-connected and connected positions, wherein in the non-connected position the first and second members are in the respective first configurations, preventing the passage of fluid through the first and second ports, respectively, and in the connected position, the first and second members are configured into the respective second configurations, allowing the aseptic passage of fluid through the first port, first aseptic passageway, second aseptic passageway and second port.

3. The aseptic connector as defined in claim 2, wherein the deflecting member is configured such that, when the first and second connectors are moved between the non-connected and the connected positions, a portion of the first connector engages the engaging portion and deflects the deflecting member between the substantially non-deflected position to the deflected position.

4. The aseptic connector as defined in claim 2, wherein in the connected position, the first fluid passageway, first port, second port, and second fluid passageway define an aseptic fluid passage sealed with respect to the ambient atmosphere for aseptic passage of fluid between the first and second connectors.

5. The aseptic connector as defined in claim 2, wherein the second connector is a female connector, and the first connector is a male connector that is received within the female connector in the connected position.

6. The aseptic connector as defined in claim 5, wherein the second connector includes a second connector housing that extends annularly about the second fluid passageway and the second member and extends axially outwardly therefrom, and the first connector includes a first connector housing that extends annularly about the first fluid passageway and the first member and extends axially outwardly therefrom, and is receivable within the second connector housing in the connected position.

7. The aseptic connector as defined in claim 1, wherein the second member in the first configuration defines a closed valve, preventing the passage of fluid through the second port, and the second member in the second configuration defines an open valve, allowing the aseptic passage of fluid through the second port.

8. The aseptic connector as defined in claim 1, wherein at least one of the first and second members is substantially dome-shaped.

9. The aseptic connector as defined in claim 1, wherein at least one of the first and second members is substantially cylindrical shaped and extends annularly about the respective at least one of the first and second ports.

10. The aseptic connector as defined in claim 1, wherein the first connector defines a second connector engaging end, and wherein all fluid-contacting surfaces of the second connector engaging end are hermetically sealed with respect to the ambient atmosphere, for preventing external contamination of said surfaces, and wherein the second connector defines a first connector engaging end, and wherein all fluid-contacting surfaces of the first connector engaging end are hermetically sealed with respect to the ambient atmosphere, for preventing external contamination of said surfaces.

11. The aseptic connector as defined in claim 1, wherein the deflecting member is resilient.

12. The aseptic connector as defined in claim 1, wherein the first member includes a deflecting member including an engaging portion and movable between a substantially non-deflected position and a deflected position, wherein in the substantially non-deflected position the first member is in its respective first configuration, and in the deflected position, the first member is in its respective second configuration.

13. The aseptic connector as defined in claim 12, wherein the deflecting member of the first member is resilient.

14. The aseptic connector as defined in claim 3, wherein the first member includes a deflecting member including an engaging portion and movable between a substantially non-deflected position and a deflected position, wherein in the substantially non-deflected position the first member is in its respective first configuration, and in the deflected position, the first member is in its respective second configuration, and when the first and second connectors are moved between the non-connected and the connected positions, the engaging portion of the second connector engages the engaging portion of the first connector and deflects the deflecting member of the first member between its substantially non-deflected position to its deflected position.

15. The aseptic connector as defined in claim 14, wherein the deflecting member of the first member is resilient.

16. The aseptic connector as defined in claim 1, wherein, in the deflected position, the deflecting member is invaginated.

17. The aseptic connector as defined in claim 1, further including a first fluid conduit connected in aseptic fluid communication with the first connector, and a second fluid conduit connected in aseptic fluid communication with the second connector.

18. The aseptic connector as defined in claim 1, wherein the first connector and the second connector are slidingly engageable with each other.

19. The aseptic connector as defined in claim 1, wherein the first connector and the second connector are releasably connectable to each other.

20. The aseptic connector as defined in claim 1, wherein the first connector includes a first housing spaced from the first member, the second connector includes a second housing spaced from the second member, and at least a portion of the first housing is receivable within the second housing to facilitate aligning the first connector and the second connector.

\* \* \* \* \*